United States Patent
Heese et al.

(10) Patent No.: US 10,872,445 B2
(45) Date of Patent: Dec. 22, 2020

(54) APPARATUS FOR TOMOSYNTHESIS IMAGE RECONSTRUCTION

(71) Applicant: KONINKLIJKE PHILIPS N.V., Eindhoven (NL)

(72) Inventors: Harald Sepp Heese, Hamburg (DE); Klaus Erhard, Hamburg (DE); Frank Bergner, Hamburg (DE); Ruediger Grewer, Hamburg (DE); Hans Barschdorf, Dassendorf (DE); Thomas Buelow, Grosshansdorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/085,615

(22) PCT Filed: Nov. 3, 2017

(86) PCT No.: PCT/EP2017/078164
§ 371 (c)(1),
(2) Date: Sep. 17, 2018

(87) PCT Pub. No.: WO2018/091285
PCT Pub. Date: May 24, 2018

(65) Prior Publication Data
US 2019/0259187 A1    Aug. 22, 2019

(30) Foreign Application Priority Data
Nov. 15, 2016 (EP) .................. 16198799

(51) Int. Cl.
*G06T 11/00* (2006.01)
*A61B 6/00* (2006.01)
(Continued)

(52) U.S. Cl.
CPC ............ *G06T 11/008* (2013.01); *A61B 6/025* (2013.01); *A61B 6/032* (2013.01); *A61B 6/12* (2013.01);
(Continued)

(58) Field of Classification Search
CPC ....... A61B 6/025; A61B 6/502; A61B 6/5258; A61B 6/12; A61B 6/032; A61B 6/5282; A61B 6/5205; A61B 6/0414; G06T 11/008
See application file for complete search history.

(56) References Cited

U.S. PATENT DOCUMENTS

2010/0128950 A1 * 5/2010 Woods ................ A61B 6/5217
                                                       382/131
2014/0050295 A1   2/2014 Dennerlein
(Continued)

FOREIGN PATENT DOCUMENTS

| DE | 102011005161 | 9/2012 |
| WO | 2005/104038 | 11/2005 |
| WO | 102011005161 | 5/2008 |

OTHER PUBLICATIONS

Ge, et al., "Digital tomosynthesis mammography: intra- and interplane artifact reduction for high-contrast objects on reconstructed slices using priori 3D geometrical information", SPIE, vol. 6512, Mar. 1, 2007.
(Continued)

*Primary Examiner* — Syed Haider
(74) *Attorney, Agent, or Firm* — Larry Liberchuk

(57) ABSTRACT

The present invention relates to an apparatus for tomosynthesis image reconstruction. It is described to provide (210) a first projection image data set and a second projection image data set acquired after acquisition of the first projection image data set, wherein, the first projection image data set comprises first projection data, and the second projection
(Continued)

image data set comprises second projection data, and wherein the first projection image data set is useable for the reconstruction of a tomosynthesis image of at least a region of interest of a body part and wherein the second projection image data set is useable for the reconstruction of a tomosynthesis image of at least the region of interest of the body part. A subset of the first projection data is selected (220). An enhanced image of at least the region of interest of the body part is reconstructed (230) on the basis of the subset of the first projection data and second projection reconstruction data comprising at least a first subset of the second projection data. Information is output (240) relating to the enhanced image of at least the region of interest of the body part.

6 Claims, 2 Drawing Sheets

(51) Int. Cl.
*A61B 6/02* (2006.01)
*A61B 6/12* (2006.01)
*A61B 6/03* (2006.01)
*A61B 6/04* (2006.01)

(52) U.S. Cl.
CPC ............ *A61B 6/502* (2013.01); *A61B 6/5205* (2013.01); *A61B 6/5258* (2013.01); *A61B 6/5282* (2013.01); *A61B 6/0414* (2013.01)

(56) References Cited

U.S. PATENT DOCUMENTS

2017/0079607 A1* 3/2017 Claus .................. A61B 6/5211
2018/0018757 A1* 1/2018 Suzuki ..................... A61B 6/03

OTHER PUBLICATIONS

Jiang, et al., "Metal Artifact Reduction of Biopsy Needles in Digital Breast Tomosynthesis"; Proceedings of the 7th Russian Bavarian Conference, Oct. 14, 2011.

Wu, et al., "Real-time out-of-plane artifact subtraction tomosynthesis imaging using prior CT for scanning beam digital x-ray system", Med. Phys. 41 (11), Nov. 2014.

* cited by examiner

APPARATUS FOR TOMOSYNTHESIS IMAGE RECONSTRUCTION

CROSS REFERENCE TO RELATED APPLICATIONS

This application is the U.S. National Phase application under 35 U.S.C. § 371 of International Application No. PCT/EP2017/078164, filed Nov. 3, 2017 published as WO 2018/091285 on May 24, 2018, which claims the benefit of European Patent Application Number 16198799.5 filed on Nov. 15, 2016. These applications are hereby incorporated by reference herein.

FIELD OF THE INVENTION

The present invention relates to an apparatus for tomosynthesis image reconstruction, a system for tomosynthesis image reconstruction, and to a method for tomosynthesis image reconstruction, as well as to a computer program element and a computer readable medium.

BACKGROUND OF THE INVENTION

Digital Breast Tomosynthesis is a rising modality for mammography screening and diagnostic follow-up. In order to additionally add value as a diagnostic modality, vendors propose to add tomosynthesis-guided biopsy as a platform feature. A biopsy needle is then used to puncture the breast tissue at the desired location with dedicated biopsy equipment (i.e. biopsy needle in biopsy needle holder mounted to patient support) after acquisition of a native tomosynthesis image of the breast to locate the lesion to be biopsied. Then a verification acquisition of another set of images conveying accurate 3D information about the location of the tip of the needle (i.e. a tomo image, or a set of 2D images that are sufficiently angulated with respect to each other) while the needle is at the expected location in order to verify that the tip of the needle is indeed at the desired location with respect to the lesion to be biopsied (verification image) is performed. Then finally a tissue sample is taken from the location of the tip of the needle.

However, in such tomosynthesis imaging there are artefacts that are due to the presence of the needle. The needle is a high contrast object, which generates streak artefacts in surrounding image regions.

Tomosynthesis systems can suffer strongly from such effects. This may be of particular severity, if potentially available projection data that is not affected by the contrast object is in fact missing due to characteristics of the acquisition geometry.

Limitations in the field-of-view due to truncated projections are also a typical limitation for boosted tomosynthesis applications which is a technique, where a sub-region of the patient anatomy is imaged with a dedicated parametrization (e.g. with higher dose, and/or higher tomographic angle) in order to better visualize structures in that sub-region for diagnostic conspicuity. Such a dedicated acquisition is always preceded by a standard acquisition in order to determine the correct sub-region.

US20140050295A1 describes a method to determine a three-dimensional target image data set showing at least one partial region of interest of an acquisition region.

SUMMARY OF THE INVENTION

Therefore, it would be advantageous to have an improved apparatus for tomosynthesis image reconstruction.

The object of the present invention is solved with the subject matter of the independent claims, wherein further embodiments are incorporated in the dependent claims. It should be noted that the following described aspects of the invention apply also for the apparatus for tomosynthesis image reconstruction, system for tomosynthesis image reconstruction and the method for tomosynthesis image reconstruction, and for the computer program element and the computer readable medium.

According to a first aspect, there is provided an apparatus for tomosynthesis image reconstruction, comprising:

an input unit;
a processing unit; and
an output unit;

The input unit is configured to provide the processing unit with a first projection image data set and a second projection image data set acquired after acquisition of the first projection image data set. The first projection image data set comprises first projection data, and the second projection image data set comprises second projection data. The first projection image data set is useable for the reconstruction of a tomosynthesis image of at least a region of interest of a body part and wherein the second projection image data set is useable for the reconstruction of a tomosynthesis image of at least the region of interest of the body part. The processing unit is configured to select a subset of the first projection data. The processing unit is also configured to reconstruct an enhanced image of at least the region of interest of the body part on the basis of the subset of the first projection data and second projection reconstruction data comprising at least a first subset of the second projection data. The subset of the first projection data is selected on the basis of projection data from the second projection data that are detected as comprising data corresponding with at least one high contrast object being present. The subset of the first projection data is used to generate synthetic forward projections, and wherein the enhanced image is reconstructed using the synthetic forward projections and the second projection reconstruction data comprising at least a first subset of the second projection data. The output unit is configured to output information relating to the enhanced image of at least the region of interest of the body part.

In this manner, a verification image acquired during tomosynthesis guided biopsies can be improved. For example, a biopsy needle and its surrounding tissue can be visualized more accurately because information acquired within a native image before the biopsy needle is present is used to enlarge the field of view of the verification, and/or remove truncation artefacts in the verification image and/or remove high contrast artefacts in the verification image. This is achieved by adding available projection data from the native image to the verification image, and/or replacing projection data in the verification image with data from the native (or pre-image).

In an example, the subset of the first projection data comprises at least one projection that is at a different projection angle to projection angles of the second projection data.

In this way, information within the first projection data (native image data) can be used to augment that within the second projection data (verification image data).

In an example, the second projection data extends over a range of projection angles, and wherein the at least one projection that is at a different projection angle to the projection angles of the second projection data is at a projection angle that is outside the range of projections of the second projection data.

In other words, the native image data extends over a wider field of view that the verification image data, and this can be used to augment the field of view in the verification image. In this way, the resultant reconstructed image will contain fewer truncation artefacts.

In an example, the processing unit is configured to determine a second subset of the second projection data that is at different to the first subset of the second projection data and wherein the second subset of the second projection data does not form part of the second projection reconstruction data.

In other words, particular projection data in the verification image are determined and these are not processed in provided the reconstruction image. In this manner, projection data that are "contaminated" can be left out of the processing.

In an example, the subset of the first projection data comprises projections of the first projection data that have corresponding projections to the projections of the second subset of the second projection data.

In other words, projections in the data set for the verification image are selected (for example because they are contaminated with image data relating to a biopsy needle) and these data are replaced with corresponding data from the native image acquired before the verification image.

In an example, the enhanced image is reconstructed using the subset of the first projection data.

In other words, the actual projections from the native image are used in reconstructing the verification image.

Synthetic projections are be generated from the native image by forward projection. This additional data is then presented to the processing unit (or reconstruction unit) together with the verification image data to further enrich the uncorrupted data for voxels. This can occur for example if potentially available projection data that is not affected by the contrast object is in fact missing due to characteristics of the acquisition geometry, such as that are affected by gaps between the sensors.

In an example, between acquisition of the first projection image data and the second projection image data a part of a biopsy equipment has been inserted into the body part, such that the second projection image data comprises image data relating to the part of a biopsy equipment.

According to a second aspect, there is provided a system for tomosynthesis image reconstruction, comprising:
an image acquisition unit; and
an apparatus for tomosynthesis image reconstruction according to the first aspect. The image acquisition unit is configured to provide the first projection image data set and the second projection image data. The output unit is configured to output the enhanced image.

According to a third aspect, there is provided a method for tomosynthesis image reconstruction, comprising:
a) providing a first projection image data set and a second projection image data set acquired after acquisition of the first projection image data set, wherein, the first projection image data set comprises first projection data, and the second projection image data set comprises second projection data, and wherein the first projection image data set is useable for the reconstruction of a tomosynthesis image of at least a region of interest of a body part and wherein the second projection image data set is useable for the reconstruction of a tomosynthesis image of at least the region of interest of the body part;
b) selecting a subset of the first projection data;
c) reconstructing an enhanced image of at least the region of interest of the body part on the basis of the subset of the first projection data and second projection reconstruction data comprising at least a first subset of the second projection data; and
d) outputting information relating to the enhanced image of at least the region of interest of the body part.

In an example, step c) comprises determining a second subset of the second projection data that is different to the first subset of the second projection data and wherein the second subset of the second projection data does not form part of the second projection reconstruction data.

In an example, step b) comprises selecting the subset of the first projection data on the basis of projection data from the second projection data that are detected as comprising data corresponding with at least one high contrast object being present.

According to another aspect, there is provided a computer program element controlling apparatus as previously described which, in the computer program element is executed by processing unit, is adapted to perform the method steps as previously described.

According to another aspect, there is provided a computer readable medium having stored computer element as previously described.

Advantageously, the benefits provided by any of the above aspects and examples equally apply to all of the other aspects and examples and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
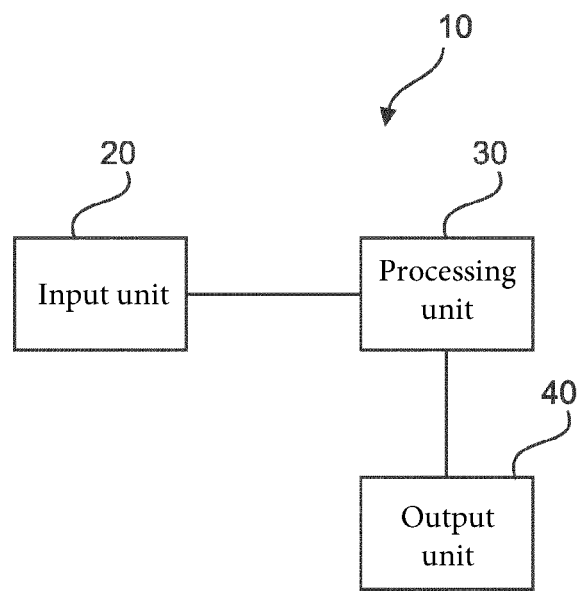
FIG. 1 shows a schematic set up of an example of an apparatus for tomosynthesis image reconstruction.

FIG. 1 shows an example of an apparatus 10 for tomosynthesis image reconstruction. The apparatus 10 comprises an input unit 20, a processing unit 30, and an output unit 40. The input unit 20 is configured to provide the processing unit with a first projection image data set and a second projection image data set acquired after acquisition of the first projection image data set, this is done via wired or wireless communication. The first projection image data set comprises first projection data, and the second projection image data set comprises second projection data. The first projection image data set is useable for the reconstruction of a tomosynthesis image of at least a region of interest of a body part, and the second projection image data set is useable for the reconstruction of a tomosynthesis image of at least the region of interest of the body part. The processing unit 30 is configured to select a subset of the first projection data. The processing unit 30 is also configured to reconstruct an enhanced image of at least the region of interest of the body part on the basis of the subset of the first projection data and second projection reconstruction data comprising at least a first subset of the second projection data. The output unit 40 is configured to output information relating to the enhanced image of at least the region of interest of the body part.

According to an example, the subset of the first projection data comprises at least one projection that is at a different projection angle to projection angles of the second projection data.

According to an example, the second projection data extends over a range of projection angles. The at least one projection that is at a different projection angle to the projection angles of the second projection data can then be at a projection angle that is outside the range of projections of the second projection data.

According to an example, the processing unit 30 is configured to determine a second subset of the second projection data that is different to the first subset of the second projection data. The second subset of the second projection data does not then form part of the second projection reconstruction data.

According to an example, the subset of the first projection data comprises projections of the first projection data that have corresponding projections to the projections of the second subset of the second projection data.

According to an example, the subset of the first projection data is selected on the basis of projection data from the second projection data that are detected as comprising data corresponding with at least one high contrast object being present.

According to an example, the enhanced image is reconstructed using the subset of the first projection data.

According to an example, the subset of the first projection data is used to generate synthetic forward projections. The enhanced image can then be reconstructed using the synthetic forward projections and the second projection reconstruction data comprising at least a first subset of the second projection data.

According to an example, between acquisition of the first projection image data and the second projection image data a part of a biopsy equipment has been inserted into the body part. The second projection image data can then comprise image data relating to the part of a biopsy equipment.

In an example, the part of the biopsy equipment is a biopsy needle.

Figure 2:
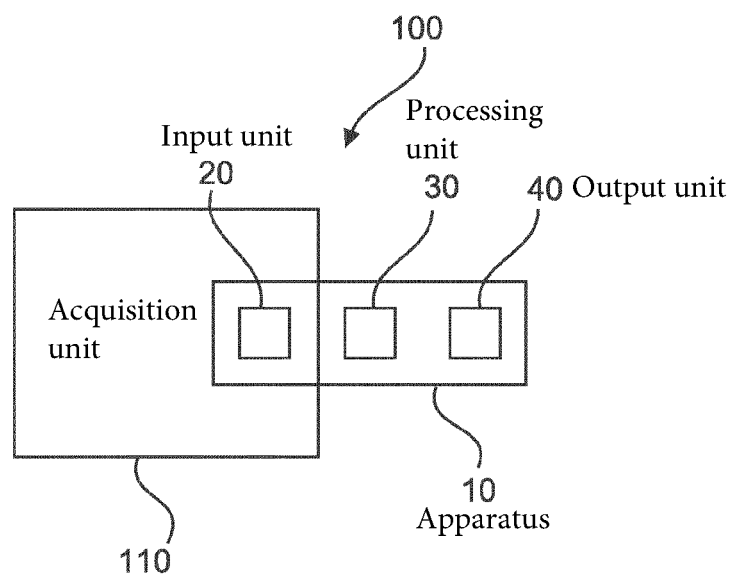
FIG. 2 shows a schematic set up of an example of a system for tomosynthesis image reconstruction.

FIG. 2 shows an example of a system 100 for tomosynthesis image reconstruction. The system 100 comprises an image acquisition unit 110, and an apparatus 10 for tomosynthesis image reconstruction as described with respect to FIG. 1. The image acquisition unit 110 is configured to provide the first projection image data set and the second projection image data. The output unit 40 is configured to output the enhanced image.

Figure 3:
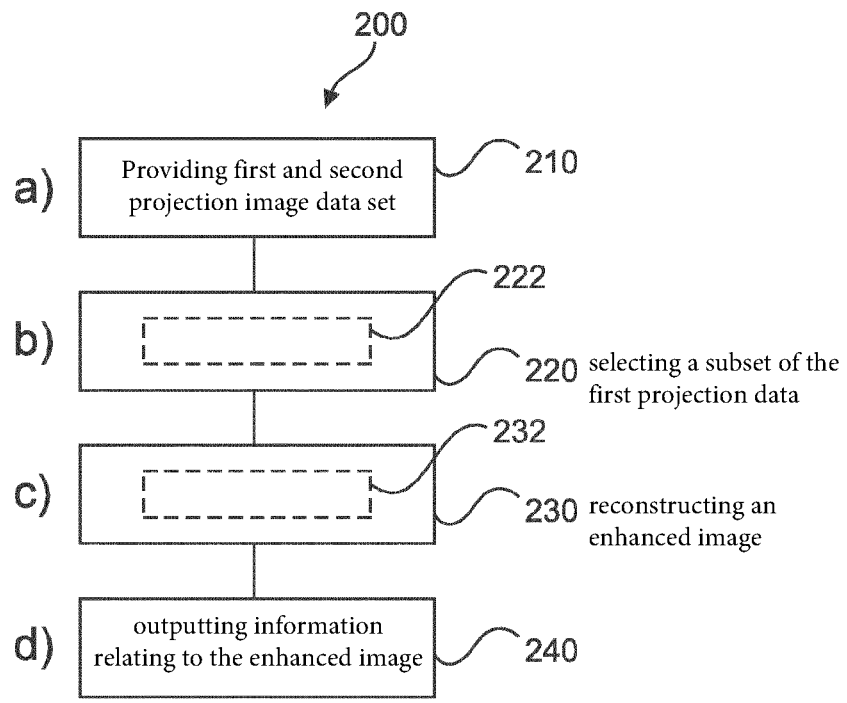
FIG. 3 shows a method for tomosynthesis image reconstruction.

FIG. 3 shows a method 200 for tomosynthesis image reconstruction in its basic steps. The method 200 comprises:

in a providing step 210, also referred to as step a), providing a first projection image data set and a second projection image data set acquired after acquisition of the first projection image data set, wherein, the first projection image data set comprises first projection data, and the second projection image data set comprises second projection data, and wherein the first projection image data set is useable for the reconstruction of a tomosynthesis image of at least a region of interest of a body part and wherein the second projection image data set is useable for the reconstruction of a tomosynthesis image of at least the region of interest of the body part;

in a selecting step 220, also referred to as step b), selecting a subset of the first projection data;

in a reconstructing step 230, also referred to as step c), reconstructing an enhanced image of at least the region of interest of the body part on the basis of the subset of the first projection data and second projection reconstruction data comprising at least a first subset of the second projection data; and in an outputting step 240, also referred to as step d), outputting information relating to the enhanced image of at least the region of interest of the body part.

In an example, in step a) the providing is from an input unit 20 to a processing unit 30.

In an example, in step b) the selecting is carried out by the processing unit 30.

In an example, in step c) the reconstructing is carried out by the processing unit.

In an example, in an example in step d) the outputting is carried out by an output unit 40.

In an example, the subset of the first projection data comprises at least one projection that is at a different projection angle to projection angles of the second projection data.

In an example, the first projection data extends over a range of projection angles, and wherein the at least one projection that is at a different projection angle to the projection angles of the second projection data is at a projection angle that is outside the range of projections of the second projection data.

According to an example, step c) comprises determining 232 a second subset of the second projection data that is different to the first subset of the second projection data and wherein the second subset of the second projection data does not form part of the second projection reconstruction data.

In an example, the subset of the first projection data comprises projections of the first projection data that have corresponding projections to the projections of the second subset of the second projection data.

According to an example, step b) comprises selecting 222 the subset of the first projection data on the basis of projection data from the second projection data that are detected as comprising data corresponding with at least one high contrast object being present.

In an example, the incorporation subset of the first projection data is the same as the subset of the first projection data.

In an example, the incorporation subset of the first projection data is generated as synthetic forward projections on the basis of the subset of the first projection data.

In an example, between acquiring the first projection image data and the second projection image data a part of a biopsy equipment has been inserted into the body part, such that the second projection image data comprises image data relating to the part of a biopsy equipment.

Figure 4:
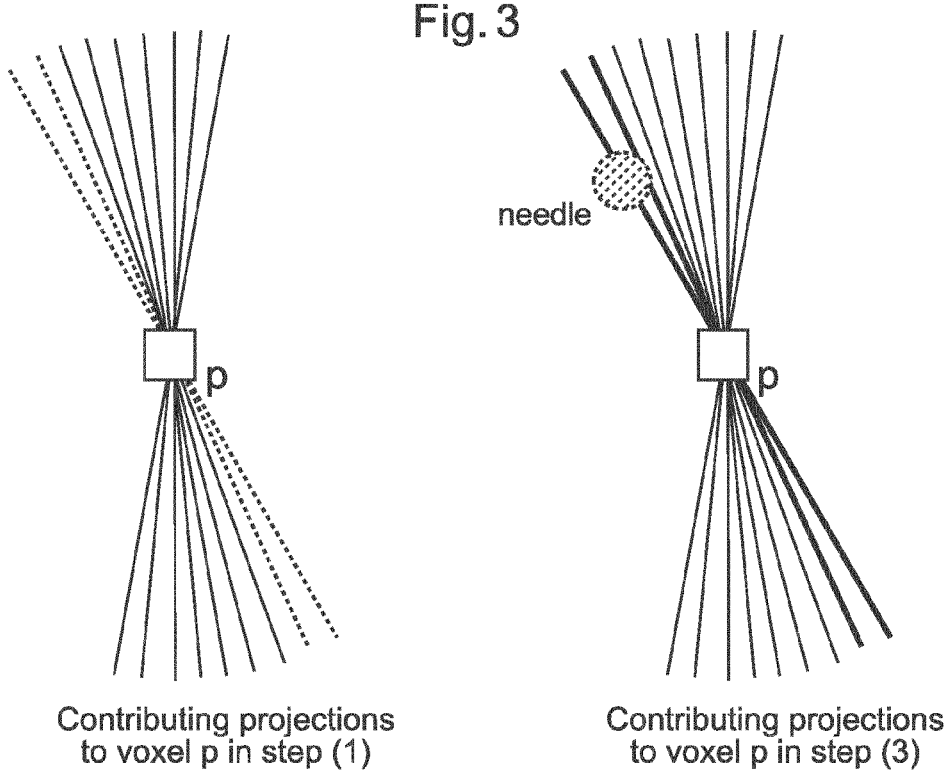
FIG. 4 shows a schematic representation of an example for the reduction of streak artifacts from a needle for the apparatus, system and method for tomosynthesis image reconstruction.

The apparatus, system and method for tomosynthesis image reconstruction are now described in further detail with respect to FIG. 4.

As discussed above, the standard procedure for tomosynthesis-guided biopsy is to:

acquire a native tomosynthesis image of the breast to locate the lesion to be biopsied, then to puncture the breast tissue at the desired location with dedicated biopsy equipment (i.e. biopsy needle in biopsy needle holder mounted to patient support), then to acquire another set of images conveying accurate 3D information about the location of the tip of the needle (i.e. a tomo image, or a set of 2D images that are sufficiently angulated with respect to each other) while the needle is at the expected location in order to verify that the tip of the needle is indeed at the desired location with respect to the lesion to be biopsied (verification image), and finally to take a tissue sample from the location of the tip of the needle.

Also, as discussed above, boosted tomosynthesis is a technique, where a sub-region of the patient anatomy is imaged with a dedicated parametrization (e.g. with higher dose, and/or higher tomographic angle) in order to better visualize structures in that sub-region for diagnostic conspicuity. Such a dedicated acquisition is always preceded by a standard acquisition in order to determine the correct sub-region.

The apparatus, system and method for tomosynthesis image reconstruction described with respect to FIGS. 1-3 and now further described with respect to FIG. 4, addresses issues associated with image reconstruction in these processes.

FIG. 4 schematically illustrates a detailed workflow for the reduction of streak artefacts from the needle. In essence, in step 3 discussed above, contributions from corrupted projections (shown in the right hand image as the projections that interact with the needle) are replaced by corresponding un-corrupted projections from projections acquired in step 1 discussed above (shown in the left hand image as the two projections that are on the upper left and on the lower right).

In other words appropriate raw-imaging data from the native tomosynthesis acquisition of step (1) is used in order to enrich the data used for reconstruction of the verification image in step (3). In this way, a reconstruction without truncation artefacts and a large field-of-view can be obtained even if the acquisition in step (3) is limited to a substantially smaller range. With respect to artefacts originating from the presence of the needle, contributions of corrupted data from step (3) are selectively replaced for the reconstruction of non-needle voxels, through the use of corresponding un-corrupted data from step (1).

A typical system has the following components:

A tomosynthesis imaging system (e.g. Philips MicroDose S-Series);

Raw tomosynthesis imaging data (a.k.a. projection data) of the breast without the needle in place;

Raw tomosynthesis imaging data (a.k.a. projection data) of the breast with the needle in place (but with e.g. reduced coverage); and A tomosynthesis reconstruction unit that is configured to create a tomosynthesis image from the projection data.

In a one embodiment the reconstruction unit is presented with the projection data from step (3) and with additional projection data from step (1) that is outside the range of projections obtained in step (3), and reconstructs a tomosynthesis image from this data. The resulting image will contain less truncation artefacts (resp. will have a larger field-of-view) due to the additional data. As further benefits less dose is applied to the patient, and the acquisition of step (3) may be optimized towards a larger tomographic angle. Such artefact-free extension of the field-of-view is of particular benefit, when the diagnostic value of the verification image relies also on the visibility of surrounding tissue in a sufficiently large region around the lesion.

This embodiment is also applicable to boosted tomosynthesis applications.

In another embodiment, the reconstruction unit is presented with the data from step (3) and with corresponding projection data from step (1). The reconstruction unit is equipped with means for detecting projection data that is contaminated by high contrast objects, and capable of replacing the respective data by corresponding data from step (1). Such artefact-free enhancement of the verification image is of particular benefit, if the diagnostic quality relies on subtle tissue structures near the needle not being occluded by artefacts.

In a variant of the invention, synthetic projections may be generated from the images of step (1) by forward projection. This additional data is then presented to the reconstruction unit together with the data from step (3) to further enrich the uncorrupted data for voxels. This can occur for example if potentially available projection data that is not affected by the contrast object is in fact missing due to characteristics of the acquisition geometry, such as that are affected by gaps between the sensors.

Specific features are now discussed in more detail
Detection of Projection Data be Detected that are Contaminated with High Contrast Objects The location of high contrast objects in tomosynthesis volume stacks can be identified by simple image analysis means such as threshold-based segmentation, which can be further enhanced by a-priori knowledge on the object (e.g. from a database containing geometric data on the depicted object). Given such a segmentation of the true high contrast object, it can be directly computed from the acquisition geometry of the tomosynthesis acquisition for each voxel of the volume stack, if it will be contaminated, and also which of the contributions are contaminated (see FIG. 4).
Replacement of Contaminated Projections Replaced, Leaving Projections that Enable the Needle to be Seen The native acquisition happens directly before the verification acquisition with the breast being in the same compression state. It hence can be assumed that the breast tissue has not moved, and that for each contaminated contribution there is a corresponding one from the native scan which may be used as a replacement. This replacement only applies to voxel in the volume stack that have been identified to be contaminated with high contrast objects. Those voxels that are identified as the high contrast object itself (see above) will not undergo the replacement. Hence the needle will stay complete visible.
Generation of Synthetic Projections by Forward Projection of Projections from the Native Image.

Generation of forward projections is a standard procedure in reconstruction. Here, attenuation values from the volume stack are accumulated along a line (projection direction). Typically, this is done along the native directions of the acquisition. A synthetic projection now refers to creating a forward projection along directions that are not native to the acquisition. For the MicroDose system this happens when due to a gap in the detector no data is generated in an acquisition.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for tomosynthesis image reconstruction, comprising:
an image acquisition device; and
an apparatus for tomosynthesis image reconstruction, comprising:
a digital storage memory configured to store processor executable instructions; and
one or more processors configured to execute the processor executable instructions to:
receive a first projection image data set and a second projection image data set which is acquired after the first projection image data set, wherein the first projection image data set comprises first projection data, and the second projection image data set comprises second projection data, wherein the first projection image data set and the second projection image data are useable for reconstructing a tomosynthesis image of at least a region of interest of a body part;
select a first subset of the first projection data based on the second projection data comprising at least one high contrast object; and
reconstruct an enhanced image of at least the region of interest of the body part based on the first subset of the first projection data and at least a second subset of the second projection data, and wherein a part of a biopsy equipment is inserted into the body part between acquisition of the first projection image data and the second projection image data, such that the second projection image data comprises the part of the biopsy equipment;
wherein the image acquisition device is configured to provide the first projection image data set and the second projection image data.

2. An apparatus for tomosynthesis image reconstruction, comprising:
a digital storage memory configured to store processor executable instructions; and
one or more processors configured to execute the processor executable instructions to:
receive a first projection image data set and a second projection image data set which is acquired after the first projection image data set, wherein the first projection image data set comprises first projection data, and the second projection image data set comprises second projection data, wherein the first projection image data set and the second projection image set are useable for reconstructing a tomosynthesis image of at least a region of interest of a body part;
select a first subset of the first projection data based on the second projection data comprising at least one high contrast object; and
reconstruct an enhanced image of at least the region of interest of the body part based on the first subset of the first projection data and at least a second subset of the second projection data, and wherein a part of a biopsy equipment is inserted into the body part between acquisition of the first projection image data and the second projection image data, such that the second projection image data comprises the part of the biopsy equipment.

3. The apparatus according to claim 2, wherein the first subset of the first projection data comprises at least one projection that is at a different projection angle to projection angles of the second projection data.

4. The apparatus according to claim 3, wherein the second projection data extends over a range of projection angles, and wherein the at least one projection that is at a different projection angle to the projection angles of the second projection data is at a projection angle that is outside the range of projections of the second projection data.

5. A method for tomosynthesis image reconstruction, comprising:

provinding a first projection image data set and a second projection image data set which is acquired after the first projection image data set, wherein the first projection image data set comprises first projection data, and the second projection image data set comprises second projection data, wherein the first projection image data set and the second projection image set are useable for reconstructing a tomosynthesis image of at least a region of interest of a body part;

selecting a first subset of the first projection data based on the second projection data comprising at least one high contrast object; and reconstructing an enhanced image of at least the region of interest of the body part based on the first subset of the first projection data and at least a second subset of the second projection data, wherein a part of a biopsy equipment is inserted into the body part between acquisition of the first projection image data and the second projection image data, such that the second projection image data comprises the part of the biopsy equipment.

6. A non-transitory computer-readable medium having one or more executable instructions stored thereon which, when executed by at least one processor, cause the at least one processor to perform a method for tomosynthesis image reconstruction, the method comprising:

providing a first projection image data set and a second projection image data set which is acquired after the first projection image data set, wherein the first projection image data set comprises first projection data, and the second projection image data set comprises second projection data, wherein the first projection image data set and the second projection image set are useable for reconstructing a tomosynthesis image of at least a region of interest of a body part;

selecting a first subset of the first projection data based on the second projection data comprising at least one high contrast object; and reconstructing an enhanced image of at least the region of interest of the body part based on the first subset of the first projection data and at least a second subset of the second projection data, wherein a part of a biopsy equipment is inserted into the body part between acquisition of the first projection image data and the second projection image data, such that the second projection image data comprises the part of the biopsy equipment.

* * * * *